(12) United States Patent
Hayashi

(10) Patent No.: US 6,946,581 B2
(45) Date of Patent: Sep. 20, 2005

(54) BISPHENOL COMPOUND COMPOSITION HAVING EXCELLENT THERMAL STABILITY

(75) Inventor: Koichi Hayashi, Mie (JP)

(73) Assignee: Mitsubishi Chemical Corporation, Tokyo (JP)

(*) Notice: Subject to any disclaimer, the term of this patent is extended or adjusted under 35 U.S.C. 154(b) by 0 days.

(21) Appl. No.: 10/603,814

(22) Filed: Jun. 26, 2003

(65) Prior Publication Data

US 2003/0234381 A1 Dec. 25, 2003

Related U.S. Application Data

(63) Continuation of application No. PCT/JP02/00784, filed on Jan. 31, 2002.

(30) Foreign Application Priority Data

Feb. 28, 2001 (JP) ........................................ 2001-053853

(51) Int. Cl.$^7$ ............................................... C07C 37/68
(52) U.S. Cl. ...................................... 568/724; 568/728
(58) Field of Search .................................. 568/724, 728

(56) References Cited

U.S. PATENT DOCUMENTS

| 4,177,343 A | * | 12/1979 | Pannell | 528/482 |
| 4,423,252 A | * | 12/1983 | Maki et al. | 568/728 |
| 4,978,739 A | * | 12/1990 | Amone et al. | 528/271 |
| 5,336,813 A | * | 8/1994 | Cipullo et al. | 568/724 |

FOREIGN PATENT DOCUMENTS

| EP | 0 374 692 | 6/1990 |
| JP | 57-120541 | 7/1982 |
| JP | 8-3088 | 1/1996 |
| JP | 11-189561 | 7/1999 |

OTHER PUBLICATIONS

English Translation of JP–57 120541.

* cited by examiner

Primary Examiner—Michael L. Shippen
(74) Attorney, Agent, or Firm—Oblon, Spivak, McClelland, Maier & Neustadt, P.C.

(57) ABSTRACT

The purpose of the invention is to improve thermal stability of bisphenol compounds.

The resolving means of the invention is to include a pyridine compound in bisphenol compounds.

29 Claims, No Drawings

BISPHENOL COMPOUND COMPOSITION HAVING EXCELLENT THERMAL STABILITY

TECHNICAL FIELD

This invention relates to a bisphenol compound composition with improved thermal stability. The bisphenol compound composition is a compound important as a raw material of polycarbonate resins and epoxy resins.

BACKGROUND ART

It is a prior knowledge that a bisphenol compound is produced by allowing a phenol compound to react with a ketone compound in the presence of an acid catalyst. Carried out in most large scale is the production of bisphenol A from phenol and acetone, but corresponding bisphenol compounds can also be produced using phenols having a substituent group on the ring, such as cresol and the like and ketone compounds other than acetone, such as methyl ethyl ketone and the like, as the raw materials.

One of the important use of polycarbonate resins produced using bisphenol compounds as the raw material is for optical use, and products free from coloring and with excellent hue are particularly required for this use. Since bisphenol compounds are melted during the production of polycarbonate resins, in order to comply with these requirements, the bisphenol compounds as raw materials must be excellent in thermal stability so that discoloration does not occur when exposed to high temperature.

As the method for improving thermal stability of bisphenol compounds, a method in which lactic acid, malic acid, glyceric acid or the like is added to a bisphenol compound (Japanese Patent Laid-Open No. 23144/1990), a method in which an aliphatic carboxylic acid or a salt thereof is added thereto (Japanese Patent Laid-Open No. 51338/1993, 51339/1993), a method in which hydroxylamine and a salt thereof is added thereto (Japanese Patent Laid-Open No. 3088/1996) and the like are known. However, the extent of thermal stability improvement effect of bisphenol compound compositions by these methods is still unsatisfactory. Thus, the invention contemplates providing a bisphenol compound composition having excellent thermal stability.

DISCLOSURE OF THE INVENTION

According to the invention, thermal stability of a bisphenol compound can be improved by allowing the bisphenol compound to contain 1 ppt to 10 ppm of a pyridine compound calculated as pyridine.

BEST MODE FOR CARRYING OUT THE INVENTION

According to the invention, discoloration when a bisphenol compound is exposed to high temperature can be reduced by allowing the bisphenol compound to contain a pyridine compound. As the pyridine compound, any of pyridine or a substituted pyridine having a substituent group on a carbon atom of the ring can be used. As the substituted pyridine, it is desirable to use alkyl or alkenylpyridines such as 4-vinylpyridine, 2-vinylpyridine, 4-methylpyridine, 2-methylpyridine, 4-ethylpyridine, 2-ethylpyridine, 2,4-dimethylpyridine and the like; and mercaptoalkylpyridines such as 2-mercaptomethylpyridine, 3-mercaptomethylpyridine, 4-mercaptomethylpyridine, 2-(2-mercaptoethyl)pyridine, 3-(2-mercaptoethyl)pyridine, 4-(2-mercaptoethyl)pyridine, 2-(3-mercaptopropyl)pyridine, 3-(3-mercaptopropyl)pyridine, 4-(3-mercaptopropyl)pyridine, 2-(4-mercaptobutyl)pyridine, 3-(4-mercaptobutyl)pyridine, 4-(4-mercaptobutyl)pyridine and the like. In addition, 2:1 condensation products of the mercapto group of these mercaptoalkylpyridines with a ketone compound can also be used.

The pyridine compound is contained in the bisphenol compound composition to a concentration of from 1 ppt to 10 ppm calculated as pyridine. In this case, "calculated as pyridine" means that when a substituted pyridine is used, its content is calculated by regarding the substituent group as hydrogen. The thermal stability is reduced when the content of pyridine compound is too large or too small. Lower limit value of the preferred content of pyridine compound in the bisphenol compound composition is 10 ppt, more preferably 1 ppb. Also, upper limit value of the preferred content of pyridine compound in the bisphenol compound composition is 1 ppm, more preferably 100 ppb. In this case, "ppt", "ppb" and "ppm" respectively mean "part(s) per trillion ($10^{12}$) by weight", "part(s) per billion ($10^9$) by weight" and "part(s) per million ($10^6$) by weight". Also, these values are values expressed by the weight ratio of a pyridine compound to the total weight of the pyridine compound and bisphenol compound contained in the bisphenol compound composition, calculated by converting the pyridine compound to pyridine.

As occasion demands, two or more pyridine compounds may be jointly used. Inclusion of a pyridine compound in a bisphenol compound can be carried out by an optional method. For example, it can be carried out by a method in which a pyridine compound is added when a bisphenol compound is used by melting it. According to this method, the content of pyridine compound can be controlled easily at a desired value. Also, a pyridine compound can be added during the step of producing a bisphenol compound from a phenol compound and a ketone compound. By this method, however, it is difficult to control the content of pyridine compound in the product accurately.

In this connection, a method is known in which a sulfonic acid type cation exchange resin prepared by modifying a portion of its sulfonic acid groups with a mercaptoalkylpyridine is used as a catalyst for forming a bisphenol compound by condensing a phenol compound with a ketone compound, but concentration of the pyridine compound in the bisphenol compound obtained by this method is generally far lower than 1 ppt. This is because the amount of mercaptoalkylpyridine released from the catalyst during the reaction is generally extremely small per unit amount of the formed bisphenol compound, and since crystallization is carried out during a period until the bisphenol compound is obtained as a product from the reaction solution containing the bisphenol compound, concentration of the pyridine compound in the product is further reduced.

Qualitative assay of the pyridine compound in the bisphenol compound composition is not particularly limited and can be carried out by those skilled in the art by suitably combining known methods. For example, after extracting and concentrating a sample to be tested as occasion demands, it can be measured by i) a chromatography assay method such as a gas chromatography, a liquid chromatography or the like, ii) a spectrophotometry or iii) an LC-MS method wherein a liquid chromatography and a mass spectrometry are combined. Particularly, when a compound having thiol group is the object like the case of the invention, a method in which it is made into a derivative by reacting with a compound having a fluorescent group, separated by a high performance liquid chromatography (HPLC) and then analyzed by a chemiluminescence method can perform high accuracy analysis and therefore is desirable.

EXAMPLES

The following describes the invention further illustratively based on examples, but the invention is not restricted by the following examples.

Examples 1 to 4 and Comparative Example 1

50 parts by weight of commercially available bisphenol A was added to a mixed solution of 100 parts by weight of water and 45 parts by weight of ethylene glycol and dissolved therein by heating to 100° C. Thereafter, this was cooled to 65° C., and the precipitated crystals were filtered and washed with water to obtain 46 parts by weight of bisphenol A. On the other hand, a pyridine compound was added to deionized water to produce a master batch of an aqueous solution of the pyridine compound. This master batch was mixed with the purified bisphenol A in such a manner that the pyridine compound content became the value shown in Table 1, and the mixture was put into a quartz glass cell having an optical path length of 40 mm and melted by keeping it at 200° C. for 30 minutes in the air using an aluminum casting heater. After further keeping at 200° C. for 6 hours, Yellow Index (YI value) was measured and calculated in accordance with JIS K-7103. In this case, U-3000 manufactured by Hitachi, Ltd. was used as the spectrophotometer. The results are shown in Table 1.

In Comparative Example 1, purified bisphenol A with no addition (blank) was used. In this connection, the YI value after melting this bisphenol A by keeping it at 200° C. for 30 minutes was 3.2.

Comparative Example 2

2-Aminoethanethiol was added to deionized water to produce a master batch of 2-aminoethanethiol aqueous solution. This master batch was mixed with the purified bisphenol A in such a manner that the 2-aminoethanethiol concentration became 0.3 ppm, and Yellow Index (YI value) was measured and calculated after heating in the same manner as in the examples. The results are shown in Table 1.

TABLE 1

|  | Pyridine compound | Content | YI value |
| --- | --- | --- | --- |
| Example 1 | 4-(2-mercaptoethyl)pyridine | 10 ppt | 4.3 |
| Example 2 | 4-(2-mercaptoethyl)pyridine | 1 ppb | 3.9 |
| Example 3 | 4-(2-mercaptoethyl)pyridine | 1 ppm | 4.3 |
| Example 4 | 4-vinylpyridine | 1 ppm | 4.6 |
| Comparative Example 1 | — | — | 5.0 |
| Comparative Example 2 | 2-aminoethanethiol | 0.3 ppm | 6.8 |

While the invention has been described in detail and with reference to specific embodiments thereof, it will be apparent to one skilled in the art that various changes and modifications can be made therein without departing from the spirit and scope thereof.

This application is based on Japanese patent application No. 2001-053853 filed on Feb. 28, 2001, the entire contents thereof being hereby incorporated by reference.

INDUSTRIAL APPLICABILITY

When the bisphenol compound composition having excellent thermal stability obtained by the invention is used as a raw material for polycarbonate resins, the bisphenol compound does not suffer discoloration when exposed to a high temperature during production process of the polycarbonate resins, so that polycarbonate resins which are free from coloring and with excellent hue are obtained as a result. Accordingly, the bisphenol compound composition having excellent thermal stability is particularly useful as a raw material of polycarbonate resins for optical use.

What is claimed is:

1. A bisphenol compound composition having excellent thermal stability, comprising:
    a bisphenol compound; and
    a pyridine compound in an amount of from 1 ppt to 10 ppm calculated as pyridine;
    wherein said bisphenol compound composition is crystallized.

2. The bisphenol compound composition according to claim 1, wherein the pyridine compound is a mercaptoalkylpyridine.

3. The bisphenol compound composition according to claim 1, comprising the pyridine compound in an amount of 10 ppt or more calculated as pyridine.

4. The bisphenol compound composition according to claim 1, comprising the pyridine compound in an amount of 1 ppm or less calculated as pyridine.

5. A method for improving thermal stability of a bisphenol compound, comprising:
    adding from 1 ppt to 10 ppm of a pyridine compound to a purified bisphenol compound.

6. The bisphenol compound composition according to claim 1, wherein said bisphenol compound is bisphenol A.

7. The bisphenol compound composition according to claim 1, wherein said bisphenol compound is produced by reacting a phenol compound with a ketone compound in the presence of an acid catalyst.

8. The bisphenol compound composition according to claim 1, wherein said bisphenol compound is produced produced by reacting a phenol having a substituent group on the ring with a ketone.

9. The bisphenol compound composition according to claim 1, wherein said pyridine compound is pyridine or a substituted pyridine having a substituent group on a carbon atom of the ring.

10. The bisphenol compound composition according to claim 1, wherein said pyridine compound is selected from the group consisting of alkylpyridines, alkenylpyridines, mercaptoalkylpyridines and mixtures thereof.

11. The bisphenol compound composition according to claim 1, wherein said pyridine compound is selected from the group consisting of 2-mercaptomethylpyridine, 3-mercaptomethylpyridine, 4-mercaptomethylpyridine, 2-(2-mercaptoethyl)pyridine, 3-(2-mercaptoethyl)pyridine, 4-(2-mercaptoethyl)pyridine, 2-(3-mercaptopropyl)pyridine, 3-(3-mercaptopropyl)pyridine, 4-(3-mercaptopropyl)pyridine, 2-(4-mercaptobutyl)pyridine, 3-(4-mercaptobutyl)pyridine, 4-(4-mercaptobutyl)pyridine and mixtures thereof.

12. The bisphenol compound composition according to claim 1, wherein said pyridine compound is selected from the group consisting of 4-vinylpyridine, 2-vinylpyridine, 4-methylpyridine, 2-methylpyridine, 4-ethylpyridine, 2-ethylpyridine, 2,4-dimethylpyridine, and mixtures thereof.

13. The bisphenol compound composition according to claim 1, wherein said pyridine compound is selected from the group consisting of 2:1 condensation products of a mercapto group of a mercaptoalkylpyridine with a ketone compound;

wherein said mercaptoalkylpyridine is selected from the group consisting of 2-mercaptomethylpyridine, 3-mercaptomethylpyridine, 4-mercaptomethylpyridine, 2-(2-mercaptoethyl)pyridine, 3-(2-mercaptoethyl)pyridine, 4-(2-mercaptoethyl)pyridine, 2-(3-mercaptopropyl)pyridine, 3-(3-mercaptopropyl)pyridine, 4-(3-mercaptopropyl)pyridine, 2-(4-mercaptobutyl)pyridine, 3-(4-mercaptobutyl)pyridine, 4-(4-mercaptobutyl)pyridine and mixtures thereof.

14. The method according to claim 5, wherein the pyridine compound is a mercaptoalkylpyridine.

15. The method according to claim 5, comprising adding the pyridine compound in an amount of 10 ppt or more calculated as pyridine.

16. The method according to claim 5, comprising adding the pyridine compound in an amount of 1 ppm or less calculated as pyridine.

17. The method according to claim 5, wherein said bisphenol compound is bisphenol A.

18. The method according to claim 5, wherein said bisphenol compound is produced by reacting a phenol compound with a ketone compound in the presence of an acid catalyst.

19. The method according to claim 5, wherein said bisphenol compound is produced produced by reacting a phenol having a substituent group on the ring with a ketone.

20. The method according to claim 5, wherein said pyridine compound is pyridine or a substituted pyridine having a substituent group on a carbon atom of the ring.

21. The method according to claim 5, wherein said pyridine compound is selected from the group consisting of alkylpyridines, alkenylpyridines, mercaptoalkylpyridines and mixtures thereof.

22. The method according to claim 5, wherein said pyridine compound is selected from the group consisting of 2-mercaptomethylpyridine, 3-mercaptomethylpyridine, 4-mercaptomethylpyridine, 2-(2-mercaptoethyl)pyridine, 3-(2-mercaptoethyl)pyridine, 4-(2-mercaptoethyl)pyridine, 2-(3-mercaptopropyl)pyridine, 3-(3-mercaptopropyl)pyridine, 4-(3-mercaptopropyl)pyridine, 2-(4-mercaptobutyl)pyridine, 3-(4-mercaptobutyl)pyridine, 4-(4-mercaptobutyl)pyridine and mixtures thereof.

23. The method according to claim 5, wherein said pyridine compound is selected from the group consisting of 4-vinylpyridine, 2-vinylpyridine, 4-methylpyridine, 2-methylpyridine, 4-ethylpyridine, 2-ethylpyridine, 2,4-dimethylpyridine, and mixtures thereof.

24. The method according to claim 5, wherein said pyridine compound is selected from the group consisting of 2:1 condensation products of a mercapto group of a mercaptoalkylpyridine with a ketone compound;

wherein said mercaptoalkylpyridine is selected from the group consisting of 2-mercaptomethylpyridine, 3-mercaptomethylpyridine, 4-mercaptomethylpyridine, 2-(2-mercaptoethyl)pyridine, 3-(2-mercaptoethyl)pyridine, 4-(2-mercaptoethyl)pyridine, 2-(3-mercaptopropyl)pyridine, 3-(3-mercaptopropyl)pyridine, 4-(3-mercaptopropyl)pyridine, 2-(4-mercaptobutyl)pyridine, 3-(4-mercaptobutyl)pyridine, 4-(4-mercaptobutyl)pyridine and mixtures thereof.

25. The bisphenol compound composition according to claim 1, wherein said pyridine compound is 4-vinylpyridine.

26. The bisphenol compound composition according to claim 1, wherein said pyridine compound is 4-(2-mercaptoethyl)-pyridine.

27. The method according to claim 5, wherein said pyridine compound is 4-vinylpyridine.

28. The method according to claim 5, wherein said pyridine compound is 4-(2-mercaptoethyl)-pyridine.

29. A bisphenol compound composition having excellent thermal stability, comprising:

a bisphenol compound; and a pyridine compound in an amount of from 1 ppt to 10 ppm calculated as pyridine;

wherein said bisphenol compound is purified by crystallization.

* * * * *